United States Patent
Lappe et al.

(10) Patent No.: US 8,200,438 B2
(45) Date of Patent: Jun. 12, 2012

(54) METHOD AND COMPUTER PROGRAM FOR CREATING ELECTRONIC CUSTODY AND CONTROL FORMS FOR HUMAN ASSAY TEST SAMPLES

(75) Inventors: Murray Lappe, Beverly Hills, CA (US); Brad Rein, Overland Park, KS (US)

(73) Assignee: eScreen, Inc., Overland Park, KS (US)

( * ) Notice: Subject to any disclaimer, the term of this patent is extended or adjusted under 35 U.S.C. 154(b) by 0 days.

(21) Appl. No.: 10/224,233

(22) Filed: Aug. 19, 2002

(65) Prior Publication Data
US 2004/0033501 A1    Feb. 19, 2004

(51) Int. Cl.
*G01N 33/48* (2006.01)

(52) U.S. Cl. ............... 702/19; 705/2; 705/3; 726/26; 700/225; 283/67

(58) Field of Classification Search .......... 702/19; 281/900; 705/2, 3; 700/225; 726/26; 283/67
See application file for complete search history.

(56) References Cited

U.S. PATENT DOCUMENTS

| | | | |
|---|---|---|---|
| 4,878,175 A * | 10/1989 | Norden-Paul et al. | 705/2 |
| 5,876,926 A | 3/1999 | Beecham | |
| 5,997,476 A | 12/1999 | Brown | |
| 6,149,440 A * | 11/2000 | Clark et al. | 434/322 |
| 6,158,779 A | 12/2000 | Petrick | |
| 6,185,683 B1 | 2/2001 | Ginter et al. | |
| 6,300,141 B1 | 10/2001 | Segal et al. | |
| 6,376,251 B1 * | 4/2002 | Braun et al. | 436/43 |
| 6,535,129 B1 * | 3/2003 | Petrick | 340/572.1 |
| 6,602,469 B1 | 8/2003 | Maus et al. | |
| 6,702,988 B1 | 3/2004 | Sagona et al. | |
| 7,143,290 B1 | 11/2006 | Ginter et al. | |
| 2002/0076819 A1 | 6/2002 | Bowman et al. | |
| 2003/0004755 A1 * | 1/2003 | Basch et al. | 705/2 |
| 2003/0040128 A1 | 2/2003 | Meador et al. | |

FOREIGN PATENT DOCUMENTS
WO   0007013 A2   2/2000

OTHER PUBLICATIONS

Ramakrishnan, Database Management Systems, WCB/McGraw-Hill, pp. 10-11 and 32-34, 1998.*

(Continued)

*Primary Examiner* — Cheyne Ly
(74) *Attorney, Agent, or Firm* — Hovey Williams LLP

(57) ABSTRACT

A system, method, and computer program that quickly, accurately, and efficiently identifies, catalogs, and tracks human assay samples and creates documentation for the human assay samples. The computer program and method include the steps of: storing donor information in a donor information database accessible by a computer; storing client information in a client information database accessible by the computer; retrieving client information necessary to determine a type of test to be performed on a specimen; storing collection facility information in a collection facility database accessible by the computer; administering a human analyte test using the computer program to guide a collector of the specimen and identify problematic exceptions; receiving the test result electronically and storing the result in a test result database accessible by the computer; and permitting the client, Medical Review Officer, and other authorized persons to electronically access the test result via a communications network.

21 Claims, 4 Drawing Sheets

OTHER PUBLICATIONS

Author Unknown. "eScreen, Inc. Introduces First FDA-cleared Automated, Instant Drug Screening System", www.escreen.com/news/news04.htm, May 14, 2001.

Author Unknown. "eScreen, Inc. Introduces MyeScreen.com, a Web-based Reporting Solution for the Drug-Testing Industry", www.escreen.com/news/news05.htm, Apr. 24, 2001.

Stafford, Diane. "Overland Park Firm Offers System Providing Quicker Drug Test Results", *The Kansas City Star*, www.escreen.com/news/news03.htm, Apr. 11, 2001.

Non-Final Office Action dated Jun. 18, 2009, in U.S. Appl. No. 11/553,819, Applicant: Lappe, Murray.

Non-Final Office Action dated Jun. 18, 2009, in U.S. Appl. No. 11/553,836, Applicant: Lappe, Murray.

Final Office Action dated Dec. 30, 2009, in U.S. Appl. No. 11/553,819; Applicant: Lappe, Murray et al.

Final Office Action dated Jan. 11, 2010, in U.S. Appl. No. 11/553,836; Applicant: Lappe, Murray et al.

Appellant's Brief as filed on Nov. 16, 2007, in U.S. Appl. No. 10/146,597; Applicant: Basch, Russel et al.

Decision on Appeal dated Nov. 12, 2009, in U.S. Appl. No. 10/146,597; Applicant: Basch, Russel et al.

Amendment dated Apr. 30, 2010, in U.S. Appl. No. 11/553,819, filed Oct. 27, 2006; Applicant: Lappe, Murray.

Final Office Action dated Jun. 21, 2010, in U.S. Appl. No. 11/553,819, filed Oct. 27, 2006; Applicant: Lappe, Murray.

Amendment dated May 11, 2010, in U.S. Appl. No. 11/553,836, filed Oct. 27, 2006; Applicant: Lappe, Murray.

Non-Final Office Action dated Jul. 12, 2010 in U.S. Appl. No. 11/553,836, filed Oct. 27, 2006; Applicant: Lappe, Murray.

\* cited by examiner

METHOD AND COMPUTER PROGRAM FOR CREATING ELECTRONIC CUSTODY AND CONTROL FORMS FOR HUMAN ASSAY TEST SAMPLES

BACKGROUND OF THE INVENTION

1. Field of the Invention

The present invention relates to human assay testing and tracking methods. More particularly, the invention relates to a system, method, and computer program that may be used to more quickly, accurately, and efficiently catalog, test, and track human assay samples and create documentation with respect to the human assay samples.

2. Description of the Prior Art

Drug testing collection facilities spend a considerable amount of time and money ordering, storing, filing, and indexing donors and clients and tracking the custody and control of specimens provided by donors. It is very important that no mistakes are made in collecting and tracking drug tests, such as mislabeling a specimen with the incorrect donor information. Therefore, drug testing collection facilities incur great expense and time to ensure that the custody and control of specimens is well-documented, correct, and forensically defensible.

Presently, most drug testing collection facilities manage specimen collection and tracking using mostly manual pen-and-paper methods. Since a majority of drug tests are performed at the request of an employer or potential employer of the donor, often for employment or pre-employment screening, a collection facility keeps a file of each employer's information and the tests they desire to be performed. The collection facility personnel then retrieves the employer's file, looks up the testing procedures the employer desires to be performed, and manually notes the selected information on a custody and control form (CCF).

Drug testing is often a regulated service, and thus, a CCF is required, or at least preferred, for each drug test a collection facility administers. A typical CCF will include the donor's name and other donor information, the employer's name and other employer information, the name of the collection facility and other collection facility information, including the name of the collector collecting the specimen, date and time of a specimen collection, and a unique identifier identifying the specimen, such as a barcode. The CCF may also include the tests to be performed on the specimen, the results of the tests, and other identifying information. The CCF usually has multiple copies, often as many as seven, so that the donor, collection facility, employer, Medical Review Officer (MRO), and lab(s) may each receive a copy. Although most forms are a carbonless type, not all copies contain the same information. For example, the donor's name and signature is often blocked out of certain copies for confidentiality. In many cases, results may be reported to the MRO but not to the collector. This requires that each individual or business in the process is mailed, faxed, or somehow forwarded their respective copy of the CCF, often at considerable expense. Additionally, each individual or business must then file and store their respective copy of the CCF, incurring personnel expense and wasting valuable storage space.

A CCF is necessary to document and track a specimen collection process. The most important item the CCF includes is a unique identifier, which identifies the specimen. A collection facility cannot complete a specimen collection until it has a unique identifier for the specimen. Therefore, the collection facility must have a CCF that contains a unique identifying label to be placed on the specimen and linking the specimen to the donor identified on the CCF. In practice, the collection facility does not collect the specimen until the collection facility has a CCF preprinted with the unique identifier, an employer's name, and a name of the MRO who will verify a positive lab result. Therefore, in order for the collection facility to open an employer's account, the collection facility commonly has CCFs for that employer preprinted with the above information.

A lab commonly supplies CCFs to the collection facility, and it is the lab which preprints the CCFs with the unique identifying label, the employer information, and the MRO's name. Once the lab preprints the CCFs, the lab then ships the forms to the collection facility or employer, which must store the forms until used. Due to the time necessary to request CCFs from the lab, wait for the lab to print each CCF with its respective employer information, MRO name, and unique identifier, and then ship the CCFs to the collection facility, it can often take six weeks or more to open a new account and preprint CCFs for an employer, tens of thousands in some cases. During this time, none of the employer's employees can be tested using the preprinted CCFs. Consequently, the process of opening an account or changing account information is unnecessarily time consuming and costly. Additionally, it is also common for each employer to have its own CCF, such that the collection facility must order and maintain separate CCFs for each employer, thus furthering the cost and time of the testing process and creating a burdensome storage problem for collectors. A change in form graphics, MRO name, or client information results in destroying thousands of unused forms. It is estimated that nearly fifty million paper CCFs, each two to seven parts, are used each year, while as many as twenty-five million are destroyed, discarded, or never used.

A procedural example of administering a human assay test begins with the donor producing a specimen, as is the case for a urine test. The collector must inspect the specimen for evidence of adulteration and note any signs of adulteration on the CCF. The collector then determines whether the specimen is within an acceptable temperature range and notes his or her findings on the CCF. The specimen is sealed and the bar code label, which is attached to the CCF, is peeled away from the CCF and affixed to the specimen container. The donor and collector sign the CCF, certifying that the information is correct, and the donor is dismissed. The collector then tests the specimen or prepares the specimen for shipment to a lab if the specimen is to be lab tested. Once received at the lab, the specimen and CCF are inspected and the information manually recorded on the CCF is manually entered by data entry personnel. The donor information, collector information, etc. are then transferred to the Laboratory Information Management System (LIMS) so that a laboratory report contains all the appropriate CCF identifying information.

Receipt of test results and marrying results to CCFs are the most problematic and inefficient steps in the drug testing process and occur after a results is reported. Turnaround time is often problematic and an important consideration because employers typically desire to receive the test results as soon as possible. A further problem of paper CCFs is the storage, filing, and indexing of the CCFs, and the delays in remarrying the CCF copy to the lab results for record-keeping purposes. This results in delays in reporting the tests results while the CCF is searched and married to the results. An employer must then be notified of the results via phone, facsimile, mail, or even e-mail.

Another problem presented by having a paper CCF is remote specimen collection. For example, if an employer desires to administer a test on a potential employee residing in Dallas, but the employer's primary place of business is in Kansas City, and consequently, the location of a collection facility that administers tests for the employer, then the employer must either transport the potential employee to Kansas City to produce a specimen, or the collection facility must mail a CCF to a collection facility in Dallas, so that a test can be administered and reported to the proper authorized contact. This process is time-consuming and expensive and could be remedied with the present invention.

SUMMARY OF THE INVENTION

The present invention solves the above-described limitations and provides a distinct advance in the art of identifying, cataloging, and tracking human analyte samples and creating documentation with respect to the human assay samples. Particularly, the invention provides a system, method, and computer program that may be used to more quickly, accurately, and efficiently catalog donors and clients, test donors for drugs, alcohol, and/or other substances or conditions, track specimens discarded and/or sent to a lab for further testing, and create an electronic Custody and Control form (CCF) that documents a particular specimen collection process. Furthermore, the CCF can be transmitted electronically, and the computer program can search and marry the CCF to the drug test results. Additionally, many aspects of the present invention may be used for identifying, cataloging, and tracking other items.

One aspect of the present invention includes a computer program and method operable to assist a collection facility in cataloging donors and clients and administering drug tests. The invention also assists the lab by pre-accessing donor information and employer information such that the results can be quickly and efficiently linked to the original CCF documentation and assists a Medical Review Officer in evaluating and verifying lab results quickly and efficiently.

The method of administering a test broadly includes three steps: (1) collecting a specimen to be tested and creating a CCF for the specimen; (2) analyzing the specimen; and (3) medically reviewing and reporting the test result to the client. Collecting a specimen and creating a CCF for the specimen broadly includes the steps of: storing client information in a client database accessible by the computer; storing donor information in a donor database accessible by a computer; storing collection facility information in a collection facility database accessible by the computer; collecting a human analyte specimen from the donor; identifying the specimen using a unique identifier; entering the unique identifier into the computer; storing the unique identifier in a database accessible by the computer; and creating a forensically defensible document, namely the CCF, which includes the donor information, the client information, the collection facility information, the unique identifier, and other identifying information.

Analyzing a specimen broadly includes the steps of: aliquotting a portion of the specimen and applying the portion locally to an analytical device that produces a test result; receiving the test result electronically from an instant testing device and storing the test result in a test result database accessible by the computer; or preparing the specimen for shipment to a lab to be tested, receiving the test result electronically from the lab, and storing the test result in a test result database accessible by the computer.

Reviewing and reporting the test result broadly includes the steps of: determining whether the test result is positive or negative; permitting the Medical Review Officer to verify the test result, if the test result is positive, by accessing the test result via a communications network; and once verified, permitting a client or other authorized person to electronically access the test result via the communications network.

In preferred forms, a client can access a test result and CCF documentation via the Internet, or other electronic means, quickly and without paper. For example, once the test result for a specimen is reported, either electronically from a lab or using a point of contact testing device, the client, such as an employer, can access a test result via the Internet. The client will not have to wait for the result/CCF to be received from the collection site, for the marrying of the documents, nor for the documents to be sent via mail, facsimile, telephone, or otherwise. Additionally, a collection facility personnel will not have to manually transmit each test result to the various people or entities that desire the result.

Another aspect of the present invention includes a computer program and method for electronically creating a Custody and Control form (CCF) for tracking the specimen. Once the specimen is collected, the specimen is labeled with a unique identifier. The computer program of the present invention is then operable to create the CCF using the unique identifier of the specimen. Therefore, unlike the prior art, the collection facility can administer a test without using a pre-printed paper CCF.

The CCF includes information such as the donor information, the client information, the collection facility's information, the unique identifier, as discussed above, and may include a reason for the test, a name of the Medical Review Officer (MRO), and a signature of both the donor and a collector. The CCF serves as a reference source for the collection facility and includes all information regarding the particular specimen collector and donor. The CCF also documents the specimen collection by requiring both the collector and donor's signature, which is especially important if the integrity of the specimen collection is questioned. For example, if future questions arise regarding the identity of the donor, the collection facility or MRO can refer to the CCF.

The CCF is electronically accessible by the collection facility, lab, MRO, and employer using a web-enabled or networked computer, and the computer program is operable to print the CCF locally, if needed. An advantage of the electronically-stored CCF is that the collection facility, lab, MRO, or employer do not have to manually file a paper CCF, thus reducing storage space and personnel time.

These and other important aspects of the present invention are described more fully in the detailed description below.

BRIEF DESCRIPTION OF THE DRAWING FIGURES

A preferred embodiment of the present invention is described in detail below with reference to the attached drawing figures, wherein.

DESCRIPTION OF THE PREFERRED EMBODIMENTS

Figure 1:
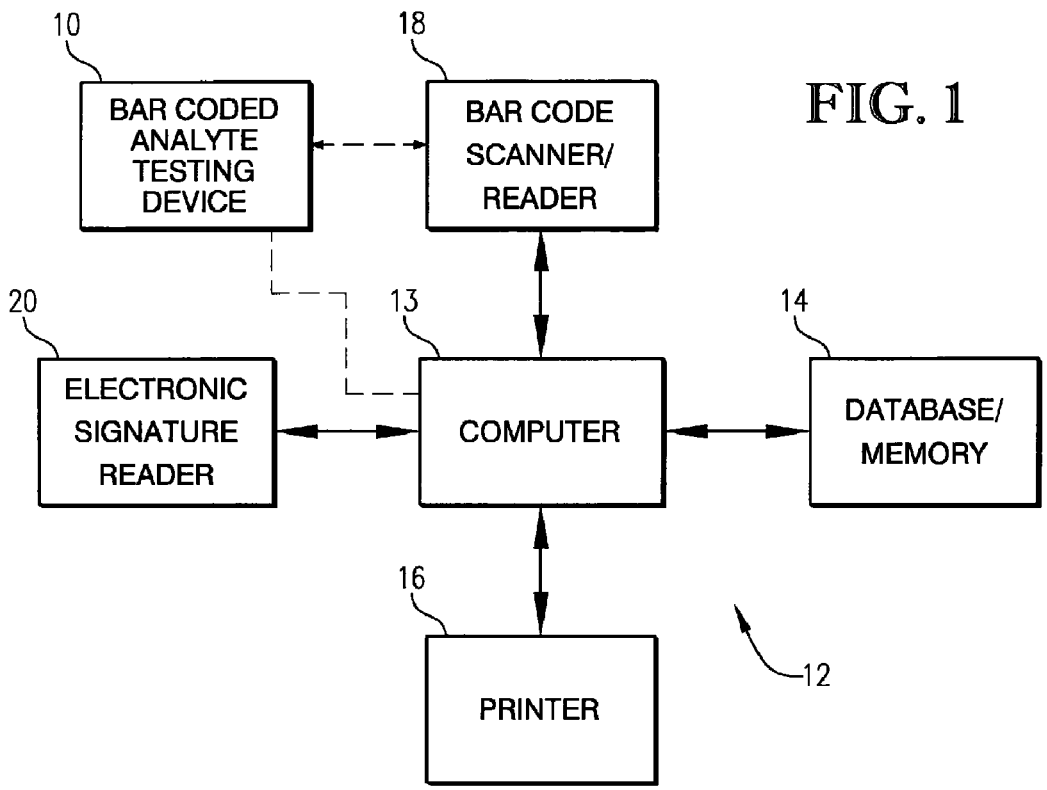
FIG. 1 is a block diagram depicting an analyte testing device and several computer equipment components that may be used to implement one or more preferred embodiments of the present invention.

The present invention is preferably implemented with an analyte testing device 10 and a computer program that operates computer equipment, broadly referred to by the numeral 12 in FIG. 1. The present invention is particularly configured for cataloging donors and clients, testing donors for drugs and/or alcohol, tracking specimens tested at the point of contact and/or sent to a lab for further testing, and creating a Custody and Control form (CCF) that documents a particular specimen collection process, but it may be used for other applications as well.

The analyte testing device 10 may be any device capable of receiving and/or testing human samples. The human sample may be urine, breath, blood, hair, saliva, sweat, etc. Examples of the analyte testing device 10 are an instant urine testing device, including a cassette tape or integrated into a specimen cup and lid, or a blood alcohol content testing device. The testing devices described herein are merely examples of testing devices that may be used to implement the present invention and may be replaced with other testing devices without departing from the scope of the present invention. Additionally, the computer program is operable to allow specimen testing by a lab.

In more detail, the specimen cup may be any device designed for receiving and/or testing a human sample, such as a urine specimen cup oral fluid collection device, or blood tube. Preferably, the specimen cup, in conjunction with the cup's lid, is capable of testing the temperature of the specimen without having to insert a thermometer into the specimen. Additionally, it is preferable that the specimen cup or lid be fitted with assaying indicia so that the urine can be instantly tested. It is also preferable, although not required, that a unique identifier, such as a bar code, be attached to or printed on the specimen cup or lid. One example of such a specimen cup and lid is sold by eScreen, Inc., of Overland Park, Kans., under the trade name eCup.

The automated urine testing device may be any instant testing device designed to test a urine specimen quickly and on-site. One example of such a testing device is sold by eScreen, Inc., of Overland Park, Kans., under the trade name eReader.

The blood alcohol content testing device may be any instant device designed to test blood or breath alcohol content quickly and on-site. One example of such a blood alcohol content testing device is sold by Draeger Safety, Inc., of Durango, Colo., under the trade name Breathalyzer 7410.

Referring now to FIG. 1, the computer equipment 12 used to implement the methods of the present invention broadly includes a computer 13 programmed as described herein, memory 14 accessible by the computer, and a printer 16. The computer equipment 12 may also include a handheld computing device containing a bar code scanner/reader 18 or a bar code scanner/reader 18 electronically connected to the computer 13 and capable of transmitting information from a bar code to the computer 13 and an electronic signature reader 20 connected to the computer 13 and capable of transmitting an electronic signature to the computer 13. The computer program and equipment 12 illustrated and described herein are merely examples of a program and equipment that may be used to implement the present invention and may be replaced with other software and computer equipment without departing from the scope of the present invention.

The computer 13 executes the computer program described herein and may be operated by a collection facility or other entity which administers human assay tests, such as an occupational health facility, an emergency room, a general care facility, a chiropractic office, a school, a court, or a police department. The computer 13 may be any computing device such as a personal computer or network server. The computer 13 may be connected to other computing devices, such as a firewall to prevent tampering with information stored on or accessible by the computer 13. The computer 13 preferably includes conventional web hosting operating software, an Internet connection such as a modem, DSL converter, or ISDN converter, and may be assigned a URL and corresponding domain name so that it can communicate and be accessed via the Internet in a conventional manner.

The memory 14 is either resident in or accessible by the computer 13 and serves as a repository for data and programs used to implement certain aspects of the present invention as described in more detail below.

Figure 2:
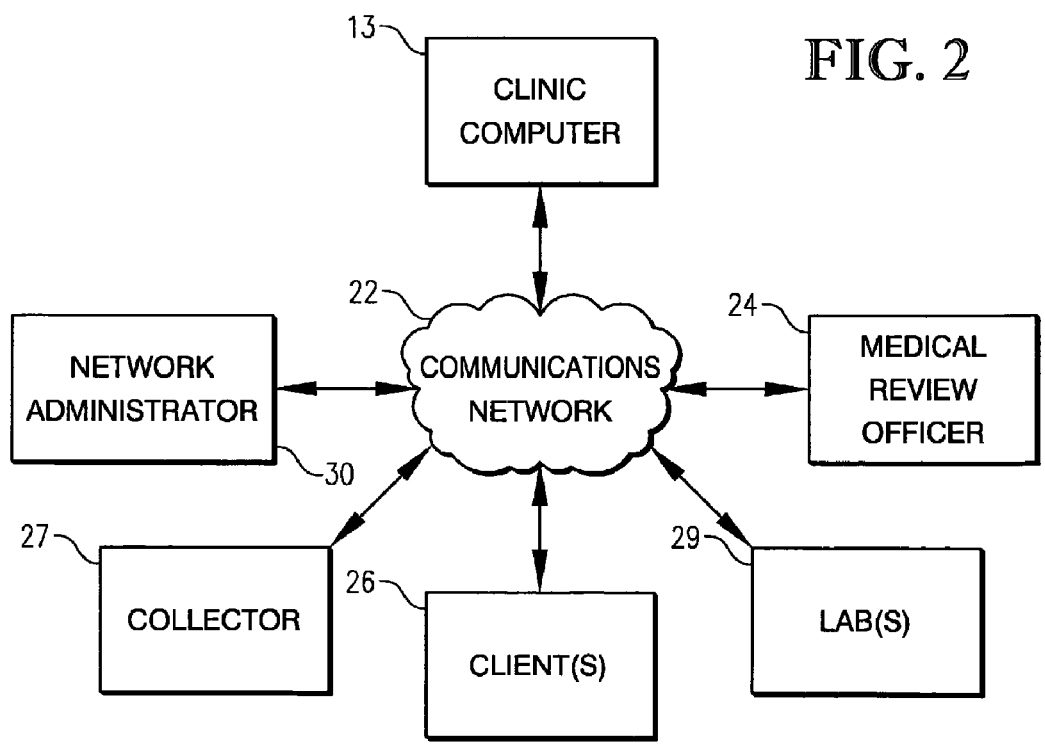
FIG. 2 is a block diagram depicting the computer equipment of FIG. 1 coupled with the computer equipment of others via a communications network.

The computer 13 can preferably receive and transmit donor information, client information, and test results to and from clients, Medical Review Officers (MROs), labs, and collection facilities. Therefore, the computer 13 is preferably capable of communicating with computing systems 13, 24, 26, 27, and 29 operated by these entities via a communications network 22, as illustrated in FIG. 2. The communications network 22 is preferably the Internet but may be any other conventional communications network such as a local area network, a wide area network, a wireless network, or an intranet.

The computer program of the present invention is stored in or on computer-readable medium residing on or accessible by the computer 13 such as the memory 14. The computer program preferably comprises an ordered listing of executable instructions for implementing logical functions in the computer 13 or the equipment coupled with the computer 13. The computer program can be embodied in any computer-readable medium for use by or in connection with an instruction execution system, apparatus, or device, such as a computer-based system, processor-containing system, or other system that can retrieve the instructions from the instruction execution system, apparatus, or device, and execute the instructions. In the context of this application, a "computer-readable medium" can be any means that can contain, store, communicate, propagate or transport the program for use by or in connection with the instruction execution system, apparatus, or device. The computer-readable medium can be, for example, but not limited to, an electronic, magnetic, optical, electromagnetic, infrared, or semi-conductor system, apparatus, device or propagation medium. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM). The computer-readable medium could even be paper or another suitable medium upon which the program is printed, as the program can be electronically captured, via for instance, optical scanning of the paper or other medium, then compiled, interpreted, or otherwise processed in a suitable manner, if necessary, and then stored in a computer memory.

The printer 16 is coupled with the computer 13 and is provided for printing forms, certificates, or reports as described in more detail below. The printer 16 may be any conventional printer, such as a laser printer or ink jet printer.

The handheld computing device may be any device that contains a bar code scanner/reader 18. If preferred, the bar code scanner/reader 18 is electronically attached to the computer 13 and capable of transmitting a bar code to the computer 13.

The electronic signature reader 20 may be any device that is capable of receiving a handwritten signature electronically and transmitting the electronic signature to the computer 13.

In accordance with one aspect of the invention, the computer equipment 12 and analyte testing device 10 described above are used to assist a collection facility in cataloging donors and clients, testing donors' specimens for drugs and/or alcohol, tracking specimens discarded and/or sent to a lab for further testing, and creating a Custody and Control form (CCF) that documents a particular specimen collection process. To catalog clients, a collection facility stores client information in a client database residing on the memory 14. Preferably, client information includes the client's name, billing and shipping information, office contact, and other identifiers. Once populated, the client database contains information for all clients using the collection facility's services.

The method of administering a test broadly includes three steps: (1) collecting a specimen to be tested and creating a CCF for the specimen; (2) analyzing the specimen; and (3) medically reviewing and reporting the test result to the client. Collecting a specimen and creating a CCF for the specimen broadly includes the steps of: storing donor information in a donor database accessible by a computer; storing client information in a client database accessible by the computer; storing collection facility information in a collection facility database accessible by the computer; retrieving client information necessary to determine a type of test to be performed on the specimen; selecting a reason for taking the test; administering a test using the computer program to guide a collector and identify problematic exceptions; labeling the specimen produced by the donor with a unique identifier, such as a barcode; storing the unique identifier identifying the specimen in a unique identifier database accessible by the computer; and creating a forensically defensible CCF which includes the donor information, the client information, the collection facility information, the unique identifier, and other identifying information.

Analyzing a specimen broadly includes the steps of: aliquotting a portion of the specimen and applying the portion locally to an analytical device that produces a test result; receiving the test result electronically from an instant testing device and storing the test result in a test result database accessible by the computer; or preparing the specimen for shipment to a lab to be tested, receiving the test result electronically from the lab, and storing the test result in a test result database accessible by the computer.

Reviewing and reporting the test result broadly includes the steps of: determining whether the test result is positive or negative; permitting a Medical Review Officer to verify the test result, if the test result is positive, by accessing the test result via a communications network; and permitting a client or other authorized person to electronically access the test result via the communications network.

These and other steps are described in more detail below.

Collecting a Specimen to be Tested and Creating a CCF for the Specimen

Before beginning the process of administering a test, a client account must be opened. To open a client account, client information is entered into a computer and stored in a client database residing on the computer's memory. Client information includes the name and address of the client and the type(s) of test(s) the client desires to be performed on a specimen.

Figures 3, 4:
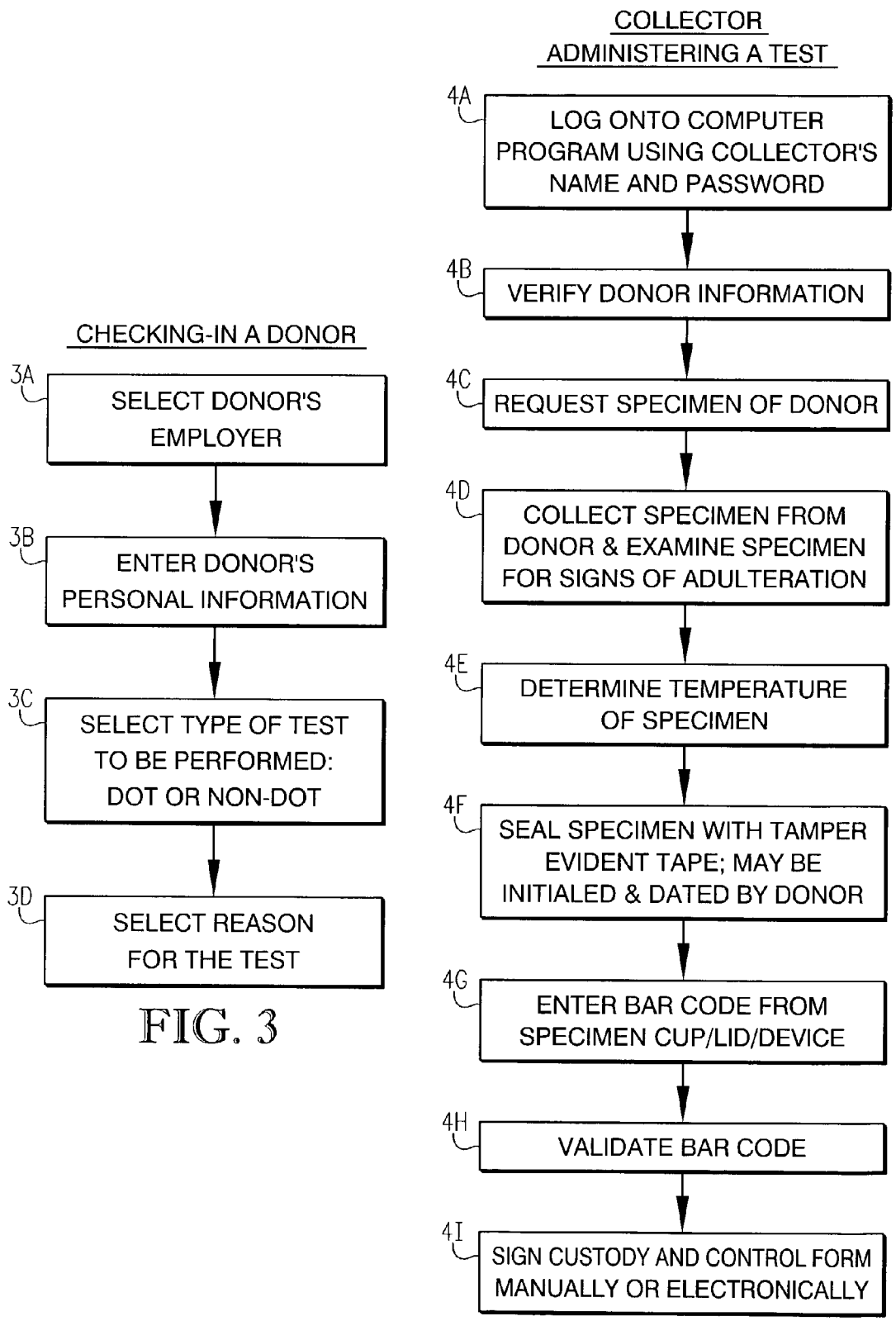
FIG. 3 is a flow diagram depicting the process of checking-in a donor using a computer program and method of the present invention.
FIG. 4 is a flow diagram depicting the process of administering a test using the computer program and method of the present invention.

To begin the process of testing a donor's specimen and tracking the donor's test results, a user, such as an employee of the collection facility, must first check-in the donor, the process of which is depicted in FIG. 3. The computer program is operable so that the user who checks-in the donor may be different than the collection facility personnel who collects the specimen from the donor. To check-in a donor, a user first selects the donor's employer from the client database, as depicted in box 3A. If the donor is a private client or is not an employee or a potential employee of an employer or previously contracted employer, then the user has the option of selecting the collection facility's house account as the employer or open a new account.

After selecting the donor's employer, the user enters donor information into the computer 13, as depicted in box 3B. The computer 13 stores the donor information in a donor database residing on the memory 14. Once populated, the donor database contains information for all donors admitted to be tested. The donor information preferably includes the donor's first and last name, the donor's birthday, the donor's social security number, and the donor's daytime and evening phone number. However, donor information sufficient to track the donor, such as social security number, is acceptable. Additionally, another embodiment of the computer program allows a client to enter the donor's information instead of the collection facility entering the donor's information.

Once the donor information has been entered, the computer program prompts the user to select the type of test(s) to be performed on the specimen, as depicted in box 3C. The computer program may be used to catalog and track donors and to catalog clients for both lab-evaluated tests and instant testing devices. Additionally, the computer program may be used with a variety of instant testing devices. In one embodiment, the user may choose either a Department of Transportation (DOT) test or a non-Department of Transportation (non-DOT) test. Since the DOT requires that all tests be lab-evaluated, as opposed to using instant testing devices, the computer program is designed so that the user must choose a lab-evaluated test for DOT tests. If the test to be given is a non-DOT test, then the user may choose either a lab test or an instant test. For both DOT and non-DOT tests, if the user desires to perform multiple tests on a specimen, the computer program is designed to allow the user the option of choosing more than one test to be performed. Additionally, since the user previously entered the donor's employer, if applicable, then the test(s) the employer desires to be performed are already selected, thus eliminating the need for the donor or user to determine which test(s) an employer wants performed.

After selecting the type of test, the computer program prompts the user to select the reason for the test, as depicted in box 3D. Possible reasons for taking a urine or breath test include pre-employment screening, post-accident, return to duty, reasonable suspicion/cause, random, etc. Once the reason for the test is selected, the donor check-in process is complete and a collector may administer a test.

The computer program is designed with several security procedures to prevent tampering of data stored on the memory 14. One such procedure requires the collector to enter his or her name and password before collecting a specimen from the donor, as depicted in box 4A. As previously noted, the collector of the specimen may be a different collection facility personnel than the user who checked-in the donor. An additional security procedure requires that the collector who begins administering a test with respect to a particular donor is also the same collector who finishes administering the test with respect to the particular donor. Therefore, the computer program is designed so that multiple collectors do not have access to the donor's information and testing status while a test is being performed. This procedural requirement protects the integrity of the system and ensures that donor information and testing results are not manipulated by human error or unauthorized personnel.

In addition to the above security procedures, the computer program stores a list of collection facility personnel using the computer program, along with each personnel's privileges, in a personnel database residing on the memory. Since a collector of a specimen must enter a password before beginning collection of the specimen, the computer program restricts the collector to administration of only those tests the collector is privileged to administer. For example, an evidential breath testing (EBT) device often requires training and certification to use. The computer program is operable to allow only those collectors who have the necessary certification to administer an EBT.

After at least one donor is checked-in, as described above, a collection facility personnel may begin administering a test, the process of which is depicted in FIG. 4. The collector must first log onto the computer program, as depicted in box 4A. Next, the collector must verify the donor's information, as depicted in box 4B, by cross-referencing the donor's information with preferably the donor's Driver's License, Identification Card, passport, or other identifier and the donor's Social Security Card. As previously noted, the computer program is operable to test and track urine, breath, blood, hair, saliva, sweat, etc. To administer a urine test, the collector gives the donor a cup and requests the donor to provide a specimen, as depicted in box 4C. Once the donor has provided a sufficient specimen, the collector inspects the specimen for signs or indications of adulteration, such as unusual odor, unusual color, etc., as depicted in box 4D. The computer program prompts the collector to indicate any signs or indications of adulteration. If the specimen does have signs or indications of adulteration, the computer program is operable to manage exceptions or deviations from the routine, as detailed below.

Next, the computer program prompts the collector to indicate whether the specimen is within an acceptable temperature range, which is approximately 90°-100° F. (32°-38° C.), as depicted in box 4E. Most urine testing devices have a temperature strip, which is easily readable, placed directly on the cup. If the specimen's temperature is not within the acceptable range, the computer program prompts the collector to withdraw a portion of the specimen and test the temperature of the withdrawn portion using a thermometer. The computer program then asks the collector one or more questions to determine whether the temperature of the specimen is within the acceptable range. If the specimen is not within the acceptable temperature range, the computer program is operable to manage exceptions or deviations from the routine, as detailed below.

After the collector inspects the specimen for signs of adulteration and notes the temperature range of the specimen, the collector seals the specimen, as depicted in box 4F. The computer program catalogs and tracks the specimen using a unique identifier, such as a bar code. If a bar code is already present on the specimen cup or lid, the collector scans the bar code using a bar code scanner/reader 18, as depicted in box 4G. The bar code is then electronically transmitted to a unique identifier database residing on the memory 14. If the collector does not have a bar code scanner/reader 18, the collector must manually enter the bar code into the unique identifier database. If the specimen cup or lid does not have a bar code on it, the collector has the option of placing a bar code on the specimen cup or lid and entering the bar code into the unique identifier database as described above. After the bar code is entered into the unique identifier database, either using a bar code scanner/reader 18 or manually entering the bar code, the collector is requested to validate the bar code, as depicted in box 4H. This is a security measure of the computer program designed to ensure that no specimen with that unique identifier has been previously tested. The computer program accesses the unique identifier database stored on the memory 14 and cross-references the present specimen's unique identifier with all other unique identifiers in the unique identifier database.

Figure 6:
FIG. 6 is a plan view of an electronic Custody and Control form (CCF) that may be used to electronically document and verify a specimen collection process and to obtain information regarding the donor or the specimen collection process.

After the specimen is validated, the donor is requested to sign and date an electronic Custody and Control form (CCF), as depicted in box 4I. The CCF, broadly referred to by the numeral 60 in FIG. 6, is used as a reference source for the collection facility or a lab and includes information regarding the specimen collection and donor. For example, the CCF 60 indicates whether the specimen was within an acceptable temperature range 70. Additionally, the CCF 60 is documentation and verification of the specimen collection process. For example, the donor's signature 80 on the CCF 60 evidences the donor's confirmation that the specimen collection is as documented on the CCF 60.

A CCF 60 preferably contains the following: the unique identifier 62 identifying the specimen, such as a bar code; a lab identification number and account number 64, if applicable; information regarding the client 66, such as the client's name, address and contact person; the Medical Review Officer's name 68; an indication of whether the specimen was within an acceptable temperature range 70; an indication that the donor's identification was verified 72; information regarding the type of specimen 74, such as urine, oral, blood, or breath; the reason for taking the test 76; information regarding the donor 78, such as the donor's name, social security number, date of birth, and daytime and evening phone number(s); the donor's signature 80; the collection facility's name and address 82; the name of the collector collecting the specimen 84; the signature of the collector 86; a lab personnel's signature 88, if applicable; an indication whether the test result is negative 90; and the MRO's signature 92.

An advantage of the present invention is that a preprinted paper CCF is not needed to administer a test. Unlike the prior art, the computer program is operable to electronically create a CCF 60 using the unique identifier for the specimen. Additionally, all reference information and identifying information for the specimen collection process can be electronically accessed to quickly complete the electronic CCF 60. In order to complete the CCF, the computer program is operable to electronically access the donor information database, the client information database, the collection facility database, the unique identifier database, the test result database, as detailed below, and the Medical Review Officer database, as detailed below. The computer program then automatically completes the CCF 60 using the information accessed from each of the above listed databases and stores the CCF 60 in a CCF database residing on the memory 14. Therefore, the collector does not have to manually complete the CCF 60. The computer program is operable to generate any CCF 60 from the CAC database by cross-referencing a donor's name, a donor's social security number, or a unique identifier on a completed CCF 60 with the donor information database or the unique identifier database. Additionally, the computer program is operable to print the CCF 60 if desired. For example, a CCF 60 must accompany any test sent to a lab to be tested, and thus, a printed CCF 60 is required.

The CCF 60 may be signed by the collector and donor electronically using an electronic signature reader 20. The computer program is operable to receive an electronic signature from the electronic signature reader 20 and store the electronic signature as part of the CCF 60 in the CCF database. If the CCF 60 is signed using an electronic signature, there is no need to print the CCF 60, unless the donor requests a copy. If the collection facility does not have an electronic signature reader 20, the collector has the option of printing the CCF 60 for the donor and collector's signature.

Analyzing the Specimen

Once the CCF 60 is signed and dated, the collector signs and dates the specimen in the presence of the donor, as depicted in box 4I, and the donor is dismissed. At this time, the collector tests the specimen using the analyte testing device 10 or prepares the specimen for shipment to a lab if the specimen is to be lab tested. Once the instant testing is complete, the collector enters the test result in the computer program, which stores the test result in a test result database residing on the memory 14. If the analyte testing device 10 is electronically connected to the computer 13, the computer program is operable to electronically receive the test result from the analyte testing device 10 and store the test result in the test result database. The computer program is also operable to allow a collector to perform an instant test and manually enter the test result into the test result database at a later time. If the test result is negative, the collector discards the specimen. If the test result is non-negative, the collector prepares the specimen for shipment to the lab. For a non-negative test result, it is preferable that the CCF 60 accompanies the specimen for shipment to the lab. Additionally, the computer program is operable to receive the test result from the lab electronically via the communications network 22 and to store the received test result in the test result database.

The process to administer a breath test is similar to the above-described process for administering a urine test. The primary difference between a urine test and a breath test is that for a breath test, there is no specimen for the collector to collect and handle. The collector must merely enter the result of the breath test into the computer program, which stores the test result on the test result database residing on the memory 14. The computer program then indicates whether the results are within an acceptable range.

The computer program is designed to accommodate exceptions or deviations from the above process. Possible deviations or exceptions, although not inclusive, are the following: donor has no valid identification; donor refuses to take the test; donor cannot produce a specimen or donor cannot breathe into the blood alcohol content testing device; donor does not produce enough urine to test; specimen appears adulterated; or specimen's temperature is not within the acceptable range. The computer program is also operable to accommodate a client's desire on how to manage exceptions or deviations from the above process. For example, if a donor's specimen is not within the acceptable temperature range, the client can design its computer program so that the collection facility has instructions to send the specimen to the lab.

Reviewing and Reporting the Result

Figure 5:
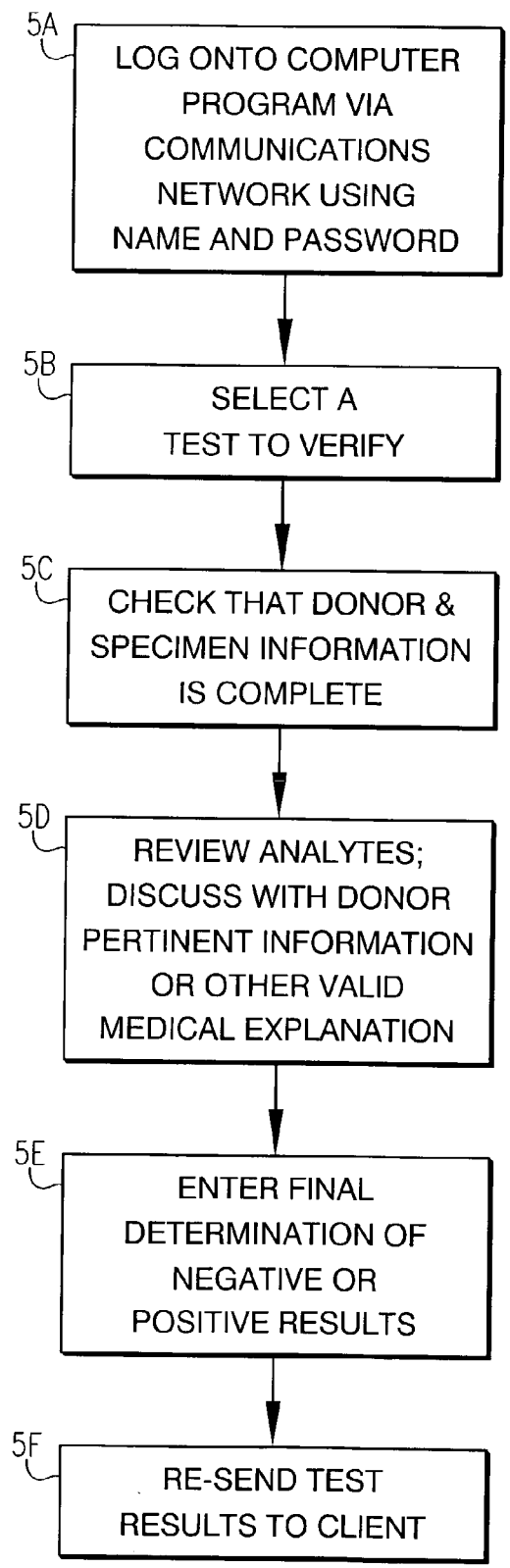
FIG. 5 is a flow diagram depicting the process of a Medical Review Officer (MRO) verifying a result using the computer program and method of the present invention.

The computer program is also operable to allow Medical Review Officers (MROs) access to lab results via the communications network 22. In a preferable embodiment, many collection facilities or employers will choose to have a medical doctor review and verify positive lab results, the process of which is depicted in FIG. 5. The MRO who reviews the lab results is listed on all CCFs for which the collection facility collects a specimen, regardless of whether the test performed is instantly tested or lab tested.

Once a test result is entered into the test result database residing on the memory 14, the MRO can access, review, and verify the test result electronically via the communications network 22. To verify a test result, the MRO selects the MRO button displayed by the computer program. The computer program then prompts the MRO to enter his or her name and password, as depicted in box 5A. Once logged onto the computer program, the computer program displays a list of the lab results awaiting verification by the MRO. The MRO may then choose which lab result to verify, as depicted in box 5B. The computer program also provides the MRO with an auto-verify option that automatically verifies negative lab results. Preferably, the MRO next checks that the donor and specimen information is complete and correct for the result the MRO is verifying, as depicted in box 5C. The MRO will then be requested to review the analytes for which the specimen was tested, as depicted in box 5D.

For a test result the lab marks positive, the MRO can edit quantities and enter comments and a final determination, as depicted in box 5E. Therefore, the computer program allows the MRO the option of overturning or canceling a positive lab result. The computer program does not allow the MRO to overturn a negative lab result. If the lab detects an adulterant in a specimen, the computer program marks the test result as adulterated. Any adulterants the lab identifies are listed below the regular analytes.

Once the MRO completes verification of a specimen, the computer program gives the MRO the option of re-sending the test result to the client, as depicted in box 5F. Additionally, the computer program has the option of reverifying a specimen, which is similar to the verification process described above.

The computer program is also operable to compile and print various reports, forms, and certificates upon request. The possible reports, forms, or certificates, although not inclusive, are the following: Collection Average Wait Time report; Turnaround Time report; Specimen Results certificate; DOT Statistics report; Client Account Summary report; Test Activity report; Client List; Collections by Collector report; Shipping report; Custody and Control form; and Client Setup form. The Collection Average Wait Time report shows clients how long, on average, their employees were waiting to be tested from the time the employee checked-in to the moment the collection was complete. The Turnaround Time report shows clients how long the testing cycle takes from the time their donor checked-in at the collection facility to the time the client received the test results. The Specimen Results Certificate shows clients the official determination of a specimen. The DOT Statistics report allows a collection facility's clients to show that they are performing adequate drug tests on their employees to stay in compliance with Department of Transportation guidelines. The Client Account Summary report provides a collection facility with a summary of a client's account. The Test Activity report allows a collection facility to view and print all tests administered by the collection facility in a given date range. A Client List lists all clients and their information. A Collections by Collector report is a list of all the tests a collector administered over a given time and/or date range. A Shipping Report tells a collection facility which specimens need to be sent to which labs. The Client Setup form is for collection facility sales personnel to fill out and give to the personnel who enter new clients into the client database.

As previously noted, the computer program is operable to be connected to other computers via a communications network 22. Therefore, the computer program can share information with other providers 28, both on a local and national level, and the computer program can share information with a collection facility's clients 26. In addition, the computer program's administrator 30 can monitor all collection facilities' use and test results. In a preferable embodiment, the computer program is connected to the Internet to allow a client to electronically access a collection facility's reports regarding the test results of the client's employees or potential employees. For example, a client would be able to access a Specimen Results Certificate to obtain the official determination of a donor's test result. The computer program is also operable to exchange information via facsimile using a telephone system or via an automated voice response using a telephone system.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A method of assisting an entity in tracking the custody and control of a human analyte specimen provided by a donor, wherein a client is requesting that the donor provide the specimen so that a test of the specimen can be performed, the method comprising the steps of:
   collecting the human analyte specimen from the donor;
   storing the specimen in a container associated with a unique identifier, wherein the unique identifier is a bar code;
   entering the unique identifier into a computer by scanning the bar code with a bar code reader;
   creating a computer-generated Custody and Control Form (CCF) that associates the specimen with the donor, wherein the CCF is electronically available to the client via a web application;
   receiving an electronic signature, wherein the electronic signature is provided by the donor by applying the donor's handwritten signature to an electronic signature reader;
   storing said electronic signature as part of the CCF; and
   enabling said client access to the CCF via said web application.

2. The method as set forth in claim 1, further including the steps of:
   obtaining client information with respect to the donor from whom the specimen is collected;
   storing the client information in a computer-accessible memory;
   obtaining collection facility information about a collection facility collecting the specimen from the donor;
   storing the collection facility information in the computer-accessible memory;
   populating the CCF with the donor information, the client information, and the collection facility information; and
   permitting authorized persons to electronically access the CCF to reference information contained in the CCF.

3. The method as set forth in claim 2, the collection facility information including the collection facility's name, address, identification number, and a name of a collector collecting the specimen.

4. The method as set forth in claim 1, wherein the human analyte specimen is selected from the group consisting of urine, blood, breath, saliva, hair, and sweat.

5. The method as set forth in claim 1, wherein the unique identifier is stored in a unique identifier database.

6. The method as set forth in claim 2, the CCF further including: a Medical Review Officer's name; an indication of whether the specimen was within an acceptable temperature range; an indication that the donor's identification was verified; information regarding the type of specimen; a reason for taking the test; the donor's signature; the name of a collector collecting the specimen; and the signature of the collector.

7. The method as set forth in claim 6, wherein the CCF is electronically retrieved from the computer-accessible memory.

8. The method as set forth in claim 7, wherein the CCF is electronically accessed via a communications network.

9. The method as set forth in claim 7, wherein the CCF is electronically retrievable by cross-referencing a first or last name or a social security number of the donor with the donor information database.

10. The method as set forth in claim 5, wherein the CCF is electronically retrievable by cross-referencing the unique identifier with the unique identifier database.

11. A non-transitory computer-readable medium encoded with code segments for directing operation of at least one computer to assist an entity in tracking the custody and control of a human analyte specimen provided by a donor, wherein a client is requesting that the donor provide the specimen so that a test of the specimen can be performed, the computer-readable medium comprising:
   a code segment executed by the at least one computer for assisting a collector in collecting the human analyte specimen from the donor, wherein the specimen is stored in a container associated with a unique identifier, wherein the unique identifier is a bar code;
   a code segment executed by the at least one computer for receiving a scan of the bar code;
   a code segment executed by the computer for entering information indicative of the bar code into the computer;
   a code segment executed by the at least one computer for creating a computer-generated Custody and Control Form (CCF) that associates the specimen with the donor, wherein the CCF is electronically available to the client via a web application;
   a code segment executed by the at least one computer for receiving an electronic signature from an electronic signature reader, wherein the electronic signature is provided by a donor by signing the electronic signature reader;
   a code segment executed by the at least one computer for storing said electronic signature as part of the CCF; and
   a code segment executed by the at least one computer for enabling said client access to the CCF via said web application.

12. The computer readable-medium as set forth in claim 11, further comprising:
- a code segment executed by the at least one computer for receiving client information with respect to the donor from whom the specimen is collected;
- a code segment executed by the at least one computer for storing client information in a client information database stored on a computer-accessible memory;
- a code segment executed by the at least one computer for receiving collection facility information about a collection facility collecting the specimen from the donor;
- a code segment executed by the at least one computer for storing the collection facility information in a collection facility database stored on the computer-accessible memory; and
- a code segment executed by the computer for permitting authorized persons to electronically access the CCF to reference information contained in the CCF.

13. The computer readable-medium as set forth in claim 12, the collection facility information including the collection facility's name, address, identification number, and a name of a collector collecting the specimen.

14. The computer readable-medium as set forth in claim 11, wherein the human analyte specimen is selected from the group consisting of urine, blood, breath, saliva, hair, and sweat.

15. The computer readable-medium as set forth in claim 12, the CCF further including: a Medical Review Officer's name; an indication of whether the specimen was within an acceptable temperature range; an indication that the donor's identification was verified; information regarding the type of specimen; a reason for taking the test; the donor's signature; the name of a collector collecting the specimen; and a signature of the collector.

16. The computer readable-medium as set forth in claim 15, wherein the CCF is electronically retrieved from the computer-accessible memory.

17. The computer readable-medium as set forth in claim 16, wherein the CCF is electronically accessed via a communications network.

18. The computer readable-medium as set forth in claim 16, wherein the CCF is electronically retrievable by cross-referencing a first or last name or a social security number of the donor with the donor information database.

19. The method as claimed in claim 1, wherein the step of creating the computer-generated CCF is performed subsequent to entering the unique identifier into the computer.

20. The method as claimed in claim 1, wherein the step of creating the electronic CCF is performed subsequent to entering the unique identifier into the computer, such that the donor is not associated with the specimen container until the unique identifier is entered into the computer.

21. The computer-readable medium as set forth in claim 11, wherein the electronic signature of the donor is reproduced on the computer-generated CCF.

* * * * *